US00PP31805P2

(12) United States Plant Patent
Van Swieten

(10) Patent No.: US PP31,805 P2
(45) Date of Patent: May 26, 2020

(54) ***PHALAENOPSIS* ORCHID PLANT NAMED 'PHALGOPWIJ'**

(50) Latin Name: ***Phalaenopsis* hybrid**
Varietal Denomination: PHALGOPWIJ

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/501,573

(22) Filed: May 2, 2019

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALGOPWIJ', particularly characterized by having white, small flowers with light greenish-yellow and white lips, 2 to 5 peduncles that are medium long and moderate, leaves that are oblong, and is propagated by meristem tissue culture, is disclosed.

3 Drawing Sheets

Genus and species: *Phalaenopsis* hybrid.
Variety denomination: 'PHALGOPWIJ'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGOPWIJ'.

The new *Phalaenopsis* plant is a product of a planned breeding program conducted by the inventor in Bleiswijk, the Netherlands. The objective of this breeding program was to create a new *Phalaenopsis* plant with numerous attractive white, small flowers with light greenish-yellow and white lips, suitable for potted plant production.

The new *Phalaenopsis* plant 'PHALGOPWIJ' is a result of cross-pollination made by the inventor in April 2009 in Bleiswijk, the Netherlands, of the proprietary female, or seed parent, *Phalaenopsis* hybrid '11968-04' (unpatented) with the proprietary male, or pollen parent, *Phalaenopsis* hybrid '01-3275' (unpatented).

The new *Phalaenopsis* was selected by the inventor as a single plant within the progeny of the stated cross-pollination in a controlled greenhouse in Bleiswijk, the Netherlands, in March 2012. Asexual reproduction of the new *Phalaenopsis* plant by meristem tissue culture since 2014 in Bleiswijk, the Netherlands, has demonstrated that the new variety reproduces true to type with all of the characteristics, as herein described, firmly fixed and retained through successive generations.

Plant Breeder's Rights for this variety have been applied for in Europe on Sept. 28, 2017, by Applicant who obtained the subject matter disclosed directly from the Inventor. 'PHALGOPWIJ' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, the Netherlands, and can be used to distinguish 'PHALGOPWIJ' as a new and distinct variety of *Phalaenopsis* plant:

1) White, small flowers with light greenish-yellow and white lips;
2) 2 to 5 peduncles;
3) Peduncle is medium long and moderate; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, the Netherlands, from 46-week-old plants in February 2019. Colors in the photographs may differ from the color values cited in the detailed botanical description, which accurately describe the actual colors of the new variety.

DESCRIPTION OF THE NEW VARIETY

Figure 1:
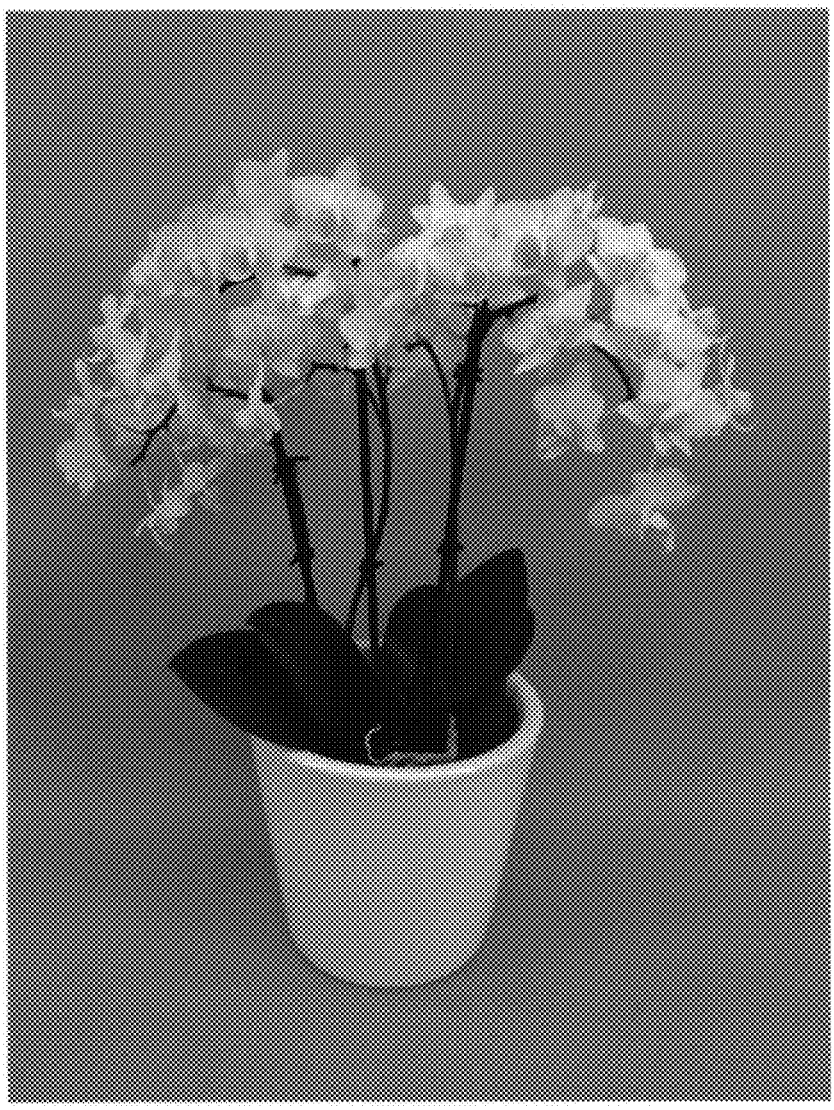
FIG. 1 shows the overall plant habit, including blooms and foliage of 'PHALGOPWIJ'.
Figure 2:
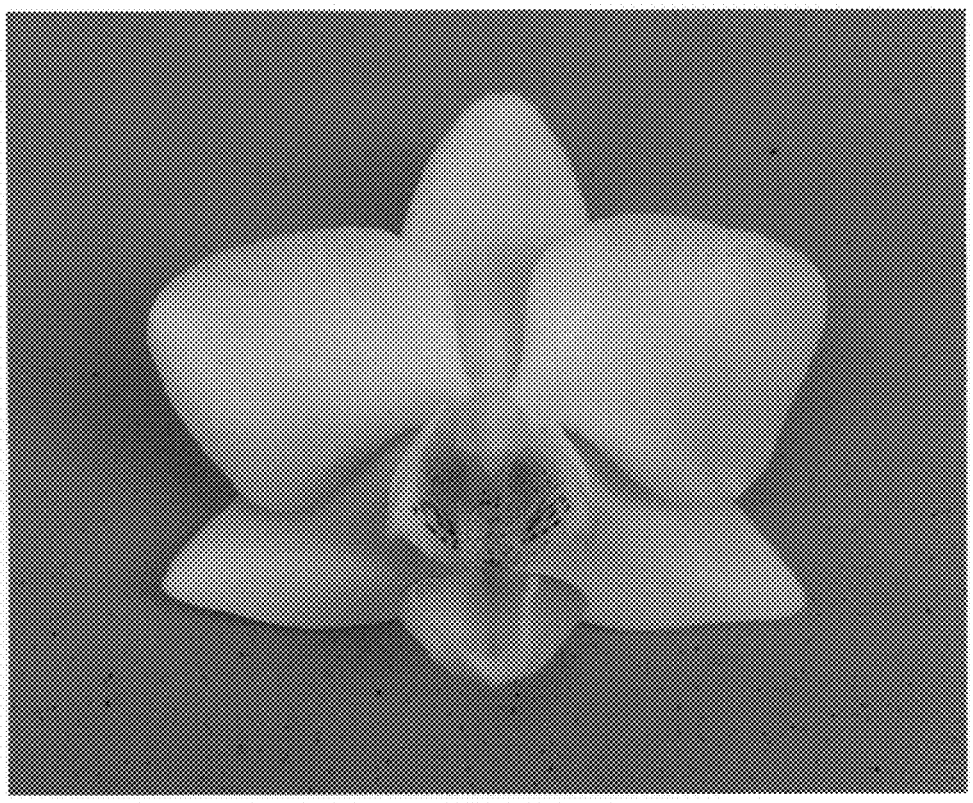
FIG. 2 shows a close-up of a flower of 'PHALGOPWIJ'.
Figure 3:
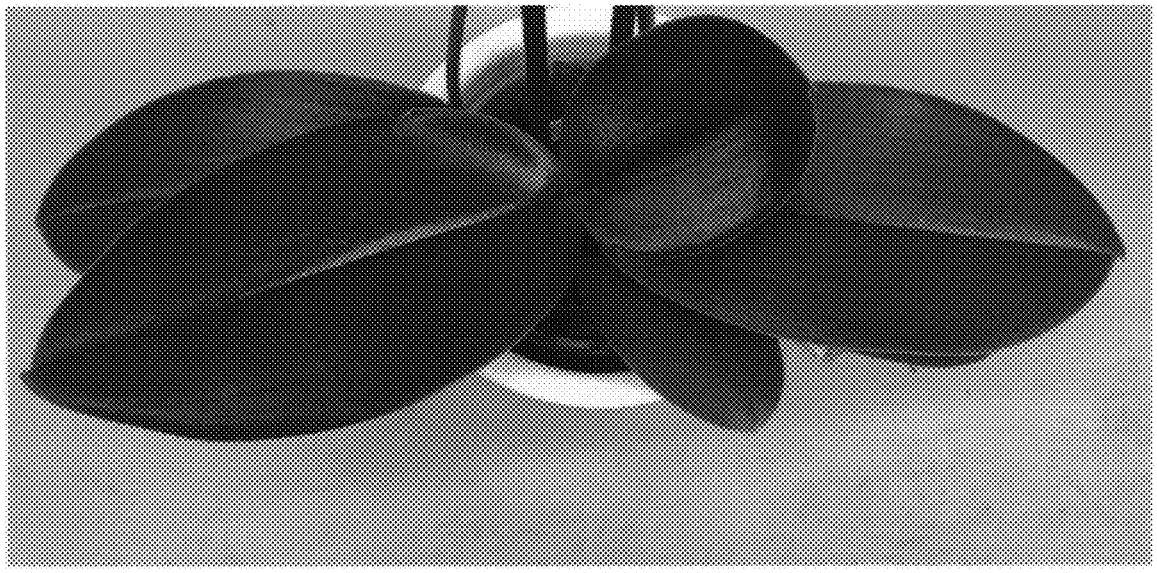
FIG. 3 shows an overhead view of the leaves of 'PHALGOPWIJ'.

The following detailed description sets forth the distinctive characteristics of 'PHALGOPWIJ'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in February 2019 on flowering plants which were planted in 9-centimeter (diameter) pots. After in-vitro propagation, the plants were grown in nursery trays for 18-20 weeks, followed by transplantation to 9-centimeter pots and grown in a greenhouse between 27° C. to 29° C. for 25 weeks, continued by a cooling period of 6 weeks between 18° C. to 20° C. and 11 weeks in a greenhouse of 21° C. Flowering occurs after 42 weeks in 9-centimeter pots.

DETAILED BOTANICAL DESCRIPTION

Classification:

*Family.*—Orchidaceae.

*Botanical.*—*Phalaenopsis* hybrid.

*Common name.*—Moth orchid.

*Variety name.*—'PHALGOPWIJ'.

Parentage:

*Female parent.*—*Phalaenopsis* cultivar '11968-04' (unpatented).

*Male parent.*—*Phalaenopsis* cultivar '01-3275' (unpatented).

Propagation:

*Type.*—Meristem tissue culture.

Roots:

*Root description.*—Greyed-green (between RHS 190B and 190C) colored roots with branching lateral roots having yellow-green (RHS 144C) colored root tips.

Plant:

*Commercial crop time to flowering.*—Following asexual propagation (in-vitro), the rooted cuttings grow for 18-20 weeks. After transplantation into 9-cm pots, the plants are finished after 40 to 42 weeks.

*Growth habit of peduncle.*—Upright to slightly pendant with raceme or panicle inflorescence.

*Height* (*from soil level to top of inflorescence*).—Approximately 34.0 cm to 39.0 cm.

*Width* (*measured from leaf tips*).—About 27.0 cm to 29.0 cm.

*Vigor.*—Moderate.

Leaves:

*Mature leaves.*—Quantity per plant: 7 to 10 leaves are produced before flowering. Length (fully expanded): 12.0 cm to 14.0 cm. Width: 6.5 cm to 7.5 cm. Shape: Oblong. Base shape: Moderately elongated. Apex: Obtuse unequal. Leaf blade angle with the petiole (measured from the horizontal position): Between 15 degrees and 30 degrees. Leaf margin: Entire. Color: Upper surface: RHS 147A. Lower surface: RHS 147B. Texture (upper surface): Rough. Thickness: 2.2 mm to 2.6 mm. Venation: Pattern: Parallel. Color of the midvein: Upper surface: RHS 147A. Lower surface: RHS 147B.

Peduncle:

*Quantity per plant.*—2 to 5.

*Number of flowers per peduncle.*—12 to 22.

*Length.*—34.0 cm to 39.0 cm.

*Diameter.*—3.7 mm to 4.1 mm.

*Strength.*—Strong.

*Aspect.*—Upright to slightly pendant.

*Texture.*—Smooth.

*Color.*—Green (RHS 146B).

*Internode length.*—3.0 cm to 4.0 cm.

Inflorescence description:

*Appearance.*—Upright to slightly pendant, raceme or panicle inflorescence with bilaterally symmetrical flowers that open in succession beginning with the lowermost flower.

*Inflorescence size.*—Height (from base to tip): 160.0 mm to 210.0 mm.

*Flowering time.*—First flowers can be expected 7 to 8 months after planting in a 9-cm pot.

*Flower.*—Height: 37.0 mm to 42.0 mm. Diameter: 43.0 mm to 48.0 mm. Depth of lip: 13.0 mm to 15.0 mm.

*Flower longevity.*—On the plant: 6 to 10 weeks.

*Fragrance.*—Absent.

*Flower bud.*—Average size: Medium. Length: 14.0 mm to 16.0 mm. Width: 11.0 mm to 13.0 mm. Shape: Egg shaped. Color: Yellow-green (RHS 150C) at the base and toward the tip (RHS 154C).

*Petals.*—Arrangement: Open/free. Shape: Semi-circular. Apex: Rounded asymmetric. Margin: Slightly undulated. Length (from base to tip): 20.0 mm to 22.0 mm. Width: 18.0 mm to 22.0 mm. Color (when fully opened): Upper surface: Basic color: White (RHS NN155C). Over color: Absent. Lower surface: Basic color: White (RHS NN155C). Over color: Absent.

*Dorsal sepal.*—Shape: Elliptic. Apex: Rounded to slightly emarginated symmetric. Margin: Entire. Length (from base to tip): 22.0 mm to 24.0 mm. Width: 26.0 mm to 28.0 mm. Color (when fully opened): Upper surface: Basic color: White (RHS NN155C). Over color: Absent. Lower surface: Basic color: White (RHS NN155C). Over color: Absent.

*Lateral sepals.*—Shape: Ovate. Apex: Obtuse asymmetric. Margin: Entire. Length (from base to tip): 21.0 mm to 23.0 mm. Width: 12.0 mm to 14.0 mm. Color (when fully opened): Upper surface: Basic color: White (RHS NN155C). Over color: Slightly light yellow-green (RHS 157C) at the base and dotted (RHS 60B). Lower surface: Basic color: White (RHS NN155C). Over color: Slightly yellow-green (RHS 157A) at the base.

*Labellum* (*lip*).—Whiskers: Present. Length of whiskers: 5.0 mm to 7.0 mm. Color of whiskers: White (RHS NN155C). Pubescence on the lip: Absent.

*Lateral lobe.*—Shape: Type V (as described in the International Union for the Protection of New Varieties of Plants (UPOV) Test Guidelines for *Phalaenopsis*); spatulate. Margin: Undulated. Length: 7.0 mm to 9.0 mm. Width: 13.0 mm to 15.0 mm. Color: White (RHS NN155C); dotted at the base (RHS 70A) and greenish-yellow (RHS 5A) on one side.

*Apical lobe.*—Shape: Trullate. Margin: Entire. Length: 15.0 mm to 17.0 mm. Width: 10.0 mm to 12.0 mm. Color: Light greenish-yellow (RHS 5C) at the base; white (RHS NN155C) toward whiskers.

*Callus.*—Average size: Small. Height: 4.0 mm to 5.0 mm. Length: 4.0 mm to 5.0 mm. Width: 3.0 mm to 4.0 mm. Color: Greenish-yellow (RHS 5A); dotted (RHS 176A).

Reproductive organs:

*Column.*—Length: 6.0 mm to 8.0 mm. Diameter: 3.4 mm to 3.6 mm. Color: White (RHS NN155C).

*Pollinia.*—Quantity: 2. Diameter: 0.8 mm to 1.0 mm. Color: Orange (RHS 24A).

*Ovary.*—Length: 8.0 mm to 10.0 mm. Diameter: 1.2 mm to 1.4 mm. Color: Light yellow-green (RHS 145C) and very light yellow-green (RHS 145D) toward the flower.

*Pedicel.*—Length: 30.0 mm to 32.0 mm. Diameter: 1.5 mm to 1.7 mm. Color: Yellow-green (RHS 144A) at the base; light yellow-green (RHS 145C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGOPWIJ' differs from female parent plant '11968-04' (unpatented) in that 'PHALGOPWIJ' has obtuse leaf apexes and spatulate lateral lobes, whereas '11968-04' has rounded leaf apexes and weakly spatulate lateral lobes.

The male parent of 'PHALGOPWIJ', cultivar '01-3275' (unpatented), is no longer in existence, therefore a meaningful comparison cannot be made.

'PHALGOPWIJ' is most similar to the commercial *Phalaenopsis* plants named 'PHALDUXI' (U.S. Plant Pat. No. 25,680) and 'PHALDUEL' (U.S. Plant Pat. No. 28,256). 'PHALGOPWIJ' differs from the commercial variety 'PHALDUXI' in that 'PHALGOPWIJ' has smaller flowers, shorter whiskers and wider leaves than 'PHALDUXI'.

'PHALGOPWIJ' differs from the commercial variety 'PHALDUEL' in that 'PHALGOPWIJ' has trullate apical lobes and small calluses, whereas 'PHALDUEL' has triangular apical lobes and medium-sized calluses. Additionally, 'PHALGOPWIJ' has smaller flowers, shorter whiskers and wider leaves than 'PHALDUEL'.

I claim:

1. A new and distinct variety of *Phalaenopsis* plant named 'PHALGOPWIJ', substantially as described and illustrated herein.

* * * * *